United States Patent
Frey, II et al.

(10) Patent No.: US 9,345,676 B2
(45) Date of Patent: *May 24, 2016

(54) METHOD OF TREATING STROKE COMPRISING ADMINISTERING METAL CHELATORS TO THE UPPER ONE-THIRD OF THE NASAL CAVITY

(71) Applicant: HealthPartners Research Foundation, Bloomington, MN (US)

(72) Inventors: William H. Frey, II, White Bear Lake, MN (US); Samuel Scott Panter, San Francisco, CA (US); Leah Ranae Bresin Hanson, Vadnais Heights, MN (US)

(73) Assignee: HealthPartners Research Foundation, Bloomington, MN (US)

(*) Notice: Subject to any disclaimer, the term of this patent is extended or adjusted under 35 U.S.C. 154(b) by 34 days.

This patent is subject to a terminal disclaimer.

(21) Appl. No.: 14/068,648

(22) Filed: Oct. 31, 2013

(65) Prior Publication Data
US 2014/0213655 A1    Jul. 31, 2014

Related U.S. Application Data

(63) Continuation of application No. 14/063,125, filed on Oct. 25, 2013, which is a continuation of application No. 12/619,009, filed on Nov. 16, 2009, now Pat. No. 8,568,691, which is a continuation of application No. 11/200,898, filed on Aug. 10, 2005, now Pat. No. 7,618,615.

(60) Provisional application No. 60/601,547, filed on Aug. 13, 2004.

(51) Int. Cl.
| A61K 31/16 | (2006.01) |
| A61K 9/00 | (2006.01) |
| A61K 47/26 | (2006.01) |
| A61K 45/06 | (2006.01) |

(52) U.S. Cl.
CPC ............. *A61K 31/16* (2013.01); *A61K 9/0043* (2013.01)

(58) Field of Classification Search
None
See application file for complete search history.

(56) References Cited

U.S. PATENT DOCUMENTS

| | | | |
|---|---|---|---|
| 2,989,437 A | 6/1961 | Wruble et al. |
| 5,135,923 A | 8/1992 | Siren |
| 5,624,898 A | 4/1997 | Frey, II |
| 5,849,290 A | 12/1998 | Brown et al. |
| 5,874,573 A | 2/1999 | Winchell et al. |
| 5,939,395 A | 8/1999 | Yu et al. |
| 6,113,906 A | 9/2000 | Greenwald et al. |
| 6,180,603 B1 | 1/2001 | Frey, II |
| 6,313,093 B1 | 11/2001 | Frey, II |
| 6,342,478 B1 | 1/2002 | Frey, II |
| 6,407,061 B1 | 6/2002 | Frey, II |
| 6,413,499 B1 | 7/2002 | Clay |
| 6,544,542 B1 | 4/2003 | Sonoke et al. |
| 6,576,660 B1 | 6/2003 | Liao et al. |
| 2001/0043915 A1 | 11/2001 | Frey, II |
| 2001/0047032 A1 | 11/2001 | Castillo et al. |
| 2002/0028786 A1 | 3/2002 | Frey, II et al. |
| 2002/0072498 A1 | 6/2002 | Frey, II |
| 2002/0082215 A1 | 6/2002 | Frey, II |
| 2002/0141971 A1 | 10/2002 | Frey, II |
| 2003/0072793 A1 | 4/2003 | Frey, II et al. |
| 2003/0133877 A1 | 7/2003 | Levin |
| 2003/0165434 A1 | 9/2003 | Reinhard et al. |
| 2003/0229025 A1 | 12/2003 | Xiao et al. |
| 2004/0101521 A1 | 5/2004 | Andersen |

FOREIGN PATENT DOCUMENTS

| WO | WO90/00057 | 1/1990 |
| WO | WO91/07947 | 6/1991 |
| WO | WO98/42275 | 10/1998 |

OTHER PUBLICATIONS

Stroke, 39: 1774-1778, 2008 [abstract only].*
Matteson MP. Annals of the New York Academy of Sciences, vol. 1012, pp. 37-50, Mar. 2004 [abstract only].*
Dezhi et al., "HIF1 alpha upregulation and neuroprotection with deferoxamine in a rat neonatal stroke model" *Pediatric Research*, 55(4): 408A (Apr. 2004).
Ross et al., Intranasal administration of interferon beta bypasses the blood-brain to target the central nervous system and cervical lymph nodes: a non-invasive treatment strategy for multiple sclerosis, *Journal of Neuroimmunology*, 151(1-2): 66-67 (Jun. 2004).
Adachi et al (Brit J Rheumatol 36:255-259, 1997).
Järvinen K and Uritti A. Duration and long-term efficacy of phenylephrine-induced reduction in the systemic absorption of ophthalmic timolol in rabbits. J Ocul. Pharmacol. 1992; 8(2):91-98; abstract only.
Vachharajani NN et al. A pharmacokinetic interactioni study between butorphanol and sumatriptan nasal sprays in healthy subjects: importance of the timing of butorphanol administration. Cephalalgia, 2002; 22:282-287.
Kruck et al., Clin Pharmacol Ther, 48(4): 439-446, Oct. 1990.
Gordon et al., Amer J Med Sci, 297(5): 280-284, May 1989.
Wang and Semenza, Blood, 82(12): 3610-3615, Dec. 15, 1993.
P. Murali Doraiswamy and Anne E. Finefrock, Metals in our minds: therapeutic implications for neurodegenerative disorders, The Lancet Neurology vol. 3, Jul. 2004 (pp. 431-434).

(Continued)

*Primary Examiner* — Vanessa L Ford
*Assistant Examiner* — Stacey N MacFarlane
(74) *Attorney, Agent, or Firm* — Barnes & Thornburg LLP (57) ABSTRACT

Methods for treating the animal central nervous system against the effects of stoke, including associated cognitive, behavioral and physical impairments. Effective amounts of therapeutic agents are administered to the upper third of the stroke patient's nasal cavity to bypass the blood-brain barrier and access the central nervous system directly to avoid unwanted and potentially lethal side effects. Therapeutic agents include those substances that interact with iron and/or copper such as iron chelators, copper chelators, and antioxidants. A particular example of a therapeutic agent is the iron chelator deferoxamine (DFO).

27 Claims, 8 Drawing Sheets

(56) References Cited

OTHER PUBLICATIONS

Maxwell and Salniknow, Cancer Biology and Therapy 3(1): 29-35. (Jan. 2004).
Brenneisen et al., The Journal of Biological Chemistry 273(9): 5279-5287. (Feb. 27, 1998).
Crapper McLachlan et al., Lancet 337(8753): 1304-1308. (Jun. 1, 1991).
Chaston and Richardson, American Journal of Hematology 73: 200-210 (2003).
King RG, Med J Aust, 142(6; 352, Mar. 18, 1985).
Youdin et al., Ann NY Acad Sci, 1012:306-325, Mar. 2004.
Lan and Jiang, J Neural Transmission, 104:469-481, 1997.
S. Talegaonkar, P.A. Mishra, Intranasal delivery: An approach to bypass the blood brain barrier, Indian J. Phermacol, Jun. 2004, vol. 36, Issue 3 140-147.
Gould et al., "Glycogen Synthase Kinase-3: A Target for Novel Bipolar Disorder Treatment," Jan. 31, 2004. The Journal of Clinical Psychiatry, vol. 65, Is. 1; p. 1021; especially abstract; p. 13, col. 2, para 3; p. 15, col. 1, para 4 to col. 2, para 1; p. 17, col. 1, para 2.
The Merck Index, Twelfth Edition, 1996, entries 3908 and 7135.
Venters Jr., Homer D. et al., "Heme from Alzheimer's brain inhibits muscarinic receptor binding via thiyl radical generation" Brain Research, 1997, 764, 93-100.
Kornberg, Arthur, et al.; "Inorganic Polyphosphate: A Molecule of Many Functions"; Annual Review Biochemistry, vol. 68: 89-125; Annual Reviews; US 1999.
Frey II, William H. et al.,; "Brain Research 714 (1996) 87-94: Endogenous Alzheimer's brain factor and oxidaized glutathione inhibit antagonist binding to the muscarinic receptor"; Elsevier Science B.V.; US 1996.
Frey II, William H. et al., "Brain Research 655 (1994) 153-160: Inhibitor of antagonist binding to the muscarinic receptor is elevated in Alzheimer's brain"; Elsevier Science B.V.; US 1994.
Otterbein, Leo E., et al.; "Invited Review: Heme Oxygenase: colors of defense against cellular stress"; The American Physiological Society; www.aiplung.org: US2000.
Rogers et al (Arch Intern Med 158:1021-1031, 1998).
van Beek et al (Biochem Biophys Res Comm 255:491-494, 1999).
Pahan et al (J Clin Invest 100:2671-2679, 1997).
Zhao et al (J Neurosci Res 52:7-16, 1998).
Fawcett et at (Brain Res 950:10-20, 2002).
Atack et al (J Neurochem 60:652-658, 1993).
Liu et al., Molecular and Cellular Biology, Sep. 1992, 3978-3990.
Frey et al., "Delivery of 1251-NGF to the Brain via the Olfactory Route", Drug Delivery, 4:87-92, 1997.
Ostovic et al (Pharm Res 10:470-472, 1993).
Rooijen (Calcif Tissue Int 52:407-410, 1993).
Body et al (Annals of Oncology, 5:359-363, 1994; Abstract Only).
Backstrom et al (J Neurosci 16:7910-7919, 1996).

\* cited by examiner

METHOD OF TREATING STROKE COMPRISING ADMINISTERING METAL CHELATORS TO THE UPPER ONE-THIRD OF THE NASAL CAVITY

CROSS-REFERENCE TO RELATED APPLICATIONS

This is a non-provisional application claiming the benefit of and priority to U.S. provisional patent application No. 60/601,547 filed Aug. 13, 2004, which is incorporated by reference.

BACKGROUND OF THE INVENTION

1. Field of the Invention

The present invention is directed to methods for preconditioning and/or providing neuroprotection to the animal central nervous system against ischemia, neurodegeneration, trauma and metal poisoning, including associated cognitive, behavioral and physical impairments.

2. Description of the Related Art

Certain medical procedures, for example coronary artery bypass graft (CABG) surgery, are associated with neurological complications. In the case of CABG, the surgery is performed on more than 800,000 patients worldwide each year. Many of the CABG procedures performed are associated with neurological complications. These complications range from stroke in up to 16% of the patients to general cognitive decline with 50% of patients having impairment post-surgery and with progressive decline occurring in some patients over the next five years. In addition, physical and behavioral impairment manifest in some CABG patients. Newman M F et al., N. Eng. J. Med. 344:395-402 (2001); Brillman J., Neurol. Clin. 11:475-495 (1993); and Seines, O. A., Ann. Thorac. Surg. 67:1669-1676 (1999) are instructive.

Originally, it was hypothesized that the neurological complications associated with CABG surgery were either procedure or patient-related. The procedure generally implicated as potentially harmful was cardiopulmonary bypass using a pump and oxygenator. However, a recent study reports no difference in cognitive outcome between groups of patients undergoing CABG surgery performed with, or without, the pump and oxygenator. Such results suggest that the neurological impairments following CABG surgery may, in fact, be patient-related and, as a result, amenable to therapeutic manipulation.

In addition, patients at risk for, or diagnosed with disorders involving neurological impairments, e.g., Alzheimer's disease, Parkinson's disease, stroke, traumatic brain injury, spinal cord injury may benefit from similar therapeutic manipulation. See Crapper McLachlan, D. R., Dalton, A. J., Kruck, T. P. A., Bell, M. Y., Smith, W. L., Kalow, W., and Andrews, D. F. Intramuscular desferrioxamine in patients with Alzheimer's disease. The Lancet 337:1304-1308, 1991.

A number of neurodegenerative disorders are known to have metal-associated pathology, i.e., resulting at least in part from metal poisoning, and may benefit from the therapeutic manipulation contemplated by embodiments of the present invention. These include AD, PD, Creutzfeldt-Jakob disease, familial amyotrophic lateral sclerosis, lewy-body dementia, carotid atherosclerosis, tardive dyskinesia, multiple sclerosis, Wilson's disease, progressive supranuclear palsy, Hallervorden-Spatz syndrome, multisystem atrophy, Huntington's disease, familial basal ganglia degeneration, Down's syndrome, cataracts, haemochromatosis, cerebral haemorrhage and head injury. See P. M. Doraiswamy and A. E. Finefrock, Metals in our minds: therapeutic implications for neurodegenerative disorders, The Lancet Neurology, Vol. 3, July 2004.

In general, ischemic conditions activate a number of genes that are important in the cellular and tissue adaptation to low oxygen conditions. These genes include erythropoietin, glucose transporters, glycolytic enzymes, and the vascular endothelial growth factor (VEGF). VEGF is a major angiogenic factor that has been shown to activate new blood vessel formation. Transcriptional up-regulation has been shown to be implicated in the induction of the VEGF gene, an action mediated by the specific binding of the hypoxia-inducible factor-1 (HIF-1) to the hypoxic response element (HRE).

The HIF-1 transcription factor is a heterodimer composed of HIF-1α and HIF-1β and regulates the adaptive response to hypoxia in animal cells. HIF-1α accumulates under hypoxic conditions, but is virtually undetectable in normal oxygen conditions. HIF-1β, on the other hand, is readily found in all cells. The HIF-1 heterodimer is believed to be neuroprotective against ischemia through the activation of EPO and VEGF.

HIF-1α has been shown in vitro to be activated by metal chelators, including both iron and copper chelating agents. A particular example of such an agent is deferoxamine (DFO), a hexadentate iron chelator, with kinetics similar to those associated with hypoxia, resulting in increased expression of HF-1 target genes, including EPO and VEGF. DFO is also known to stabilize HIF-1 subunits, possibly by chelating and inactivating the iron that plays a role in targeting the subunit for proeolytic degradation under normoxic conditions.

In vivo studies have demonstrated that DFO induces HIF-1α in neonatal and adult rats, injecting the chelator either subcutaneously (s.c.) or intraperitoneally (i.p.), typically in very high dosage. In addition, studies indicate that the following substances stimulate and/or stabilize HIF-1α: insulin, IGF-I, heregulin insulin, heregulin, TGFbeta, IL-1 beta, TNFalpha, cobalt, pyruvate, oxalacetate and lactate.

Problems exist, however, with the administration of DFO intravenously. DFO is not generally injected intravenously for at least two reasons. First, it is a small molecule and, as a result, is eliminated rapidly through the kidney. The typical plasma half-life in humans is less than 10 minutes. Second, the injection of an intravenous bolus of DFO causes acute hypotension that is rapid, may lead to shock and may be lethal. These characteristics have limited the utility of DFO in particular as a neuroprotective agent.

One published study administered DFO intranasally to iron overloaded patients. G. S. Gordon et al., Intranasal Administration of Deferoxamine to Iron Overloaded Patients, (1989) Am. J. Med. Sci. 297(5):280-284. In this particular study, DFO was administered to the patients as a nasal spray in a volume of 75 microliters per spray. Significantly, such sprays are known to deposit the drug or other substance in the lower third of the nasal cavity. This is verified by patient observations stating that a bad taste in the mouth was resulting from the drug passing through the nasopharynx and into the mouth. As a result, this study did not involve delivering the drug to the upper third of the nasal cavity. Thus, the drug would not have reached the olfactory epithelium or the olfactory nerves. As a result, delivery of the drug to the CNS would be less than optimal.

It is recognized that intranasal delivery to the CNS may occur along both the olfactory and trigeminal nerve pathways. See Thorne, R G (2004), Delivery of Insulin-Like Growth Factor-I to the Rat Brain and Spinal Cord Along Olfactory and Trigeminal Pathways Following Intranasal Administration, Neuroscience, Vol. 127, pp. 481-496. Optimal delivery taking advantage of both pathways is accomplished by administering the substance in the upper third of the nasal cavity.

Regarding Alzheimer's disease, some studies indicate that cerebral vascular problems occur first, followed by neurodegeneration in later stages of the disease. For example, see The Lancet Neurology, vol. 3, page 184-190, Jack C. de la Torre (March, 2004). Thus, it may be possible to prevent, mitigate or treat the effects of Alzheimer's disease at the appropriate disease stage through therapeutic manipulation targeted toward mitigation or prevention of cerebral ischemia or neurodegeneration.

In a published patent application, U.S. Pat. App. No. 20020028786 by William H. Frey II (also a co-inventor of the present application) entitled METHODS AND COMPOSITIONS FOR ENHANCING CELLULAR FUNCTION THROUGH PROTECTION OF TISSUE COMPONENTS, various substances are discussed that may be administered intranasally to treat various diseases and conditions. The entire contents of this reference are hereby incorporated by reference.

BRIEF SUMMARY OF THE INVENTION

Given the situation described above there is a need for a method for efficiently and safely conditioning, or preconditioning, the animal CNS to prevent or minimize cognitive, behavioral and physical impairment due to ischemia, neurodegeneration, CNS trauma and free radical damage from copper, zinc and iron. In addition, there is a need for a method for efficiently and safely conditioning and treating the animal CNS to treat existing cognitive, behavioral and physical impairment due to ischemia, neurodegeneration, CNS trauma and free radical damage from copper and iron. Further, there is a need to optimize the administration or delivery of a therapeutic agent.

Methods and pharmaceutical compositions for preconditioning the CNS to neuroprotect against, minimize and/or prevent the effects of ischemia and the cognitive, behavioral and physical impairments that often accompany ischemic episodes by stimulating and stabilizing hypoxia-inducible factor-1α (HIF-1α) are provided herein. HIF-1α is known to provide a neuroprotective benefit under ischemic conditions. Patients at risk for certain diseases or disorders that carry a concomitant risk for ischemia may benefit, e.g., those at risk for Alzheimer's disease, Parkinson's disease or stroke. Patients undergoing certain medical procedures that may result in ischemia may also benefit.

In addition, methods and compounds for treating patients that have undergone an ischemic episode to minimize the effects of the ischemia.

Initially, under a representative embodiment of the invention, the possibility of an ischemic episode or neurodegeneration is recognized. Intranasal therapeutic agent is administered to the upper third of the nasal cavity to bypass the blood-brain barrier and access the central nervous system directly to avoid unwanted and potentially damaging side effects. Therapeutic agents include those substances that may interact with iron and/or copper such as iron chelators, copper chelators, and/or antioxidants and free radical scavengers. A particular example of such therapeutic agents is the iron chelator deferoxamine (DFO). DFO may also chelate copper as well as other metals. Intranasal administration of DFO is known to stimulate and/or stabilize HIF-1α and provides an efficient and safe method for pre-conditioning the CNS to protect against cerebral ischemia. The effects of pretreating a patient, who ultimately experiences ischemia, include significant reduction of infarct volume as well as a significant decrease in weight loss following stroke.

Another embodiment of the invention provides a method and pharmaceutical compositions for treating a patient that has undergone an ischemic episode by administering at least one does of a therapeutic agent via intranasal delivery to the upper one-third of the nasal cavity. As discussed above in connection with pretreatment, metal chelators, e.g., DFO, may be used to treat a patient post-stroke. The effects of post-stroke intranasal administration of such a therapeutic agent include significant reduction of infarct volume as well as a significant decrease in weight loss following stroke.

Thus, one embodiment of the invention relates to a method and pharmaceutical compositions for preventing, minimizing and/or treating neurologic complications due to cerebral ischemia as a result of certain medical procedures. The method comprises administering at least one dose of a therapeutic agent via intranasal delivery to the upper one-third of the nasal cavity prior to undergoing a medical procedure that may result in neurologic complications.

Another embodiment of the invention relates to a method and pharmaceutical compositions for preventing, minimizing and/or treating neurologic complications due to cerebral ischemia or neural degeneration as a result of certain medical procedures. The method comprises administering at least one dose of at least one therapeutic agent via intranasal delivery to the upper one-third of the nasal cavity during, prior to and/or after undergoing a medical procedure that may result in neurologic complications. The particular therapeutic agent(s) selected may preferentially chelate iron or copper or a combination of the iron and copper, or otherwise interact with select metals or prevent oxidation/reduction cycling of iron or copper.

Yet another embodiment of the invention relates to a method and pharmaceutical compositions for decreasing weight loss encountered by patients having cerebral ischemic episode.

Another embodiment of the invention relates to a method and pharmaceutical compositions for preventing, minimizing and/or treating neurologic complications due to cerebral ischemia and/or neurodegeneration for patients at risk for, or diagnosed with, certain medical conditions such as Alzheimer's disease, Parkinson's disease, Creutzfeldt-Jakob disease, familial amyotrophic lateral sclerosis, lewy-body dementia, carotid atherosclerosis, tardive dyskinesia, multiple sclerosis, Wilson's disease, progressive supranuclear palsy, Hallervorden-Spatz syndrome, multisystem atrophy, Huntington's disease, familial basal ganglia degeneration, Down's syndrome, cataracts, haemochromatosis, cerebral hemorrhage, subarachnoic hemorrhage, head injury, and spinal cord injury.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Definitions

As used herein, "central nervous system" (CNS) refers to the brain and spinal cord and associated tissues.

An "effective amount" of agent is an amount sufficient to prevent, treat, reduce and/or ameliorate the symptoms, neuronal damage and/or underlying causes of any of the referenced disorders or diseases. In some instances, an "effective amount" is sufficient to eliminate the symptoms of those diseases and overcome the disease itself.

In the context of the present invention, the terms "treat" and "therapy" and "therapeutic" and the like refer to alleviate, slow the progression, prophylaxis, attenuation or cure of ischemia, trauma, metal poisoning or neurodegeneration.

"Prevent", as used herein, refers to putting off, delaying, slowing, inhibiting, or otherwise stopping, reducing or ameliorating the onset of ischemia, trauma, metal poisoning or neurodegeneration. It is preferred that a large enough quantity of the agent be applied in non-toxic levels in order to provide an effective level of neuroprotection. The method of the present invention may be used with any animal, such as a mammal or a bird (avian), more preferably a mammal. Poultry are a preferred bird. Exemplary mammals include, but are not limited to rats, mice, cats, dogs, horses, cows, sheep, pigs, and more preferably humans.

Thus, methods and pharmaceutical compositions are described herein that, inter alia, prevent, and/or treat neurologic complications such as cognitive, behavioral and/or physical impairment due to ischemia, neurodegeneration, trauma and metal poisoning.

An alternative to potentially lethal and generally ineffective intravenous injection of metal chelators, e.g., DFO, may be accomplished using an alternative non-invasive method to directly target the substance to the brain and thus the central nervous system (CNS). Intranasal delivery allows substances to be rapidly delivered to the central nervous system, even those that do not readily cross the blood-brain barrier by bypassing the blood-brain barrier and directly exposes the CNS to the delivered substance. In this manner, unwanted systemic side effects are reduced if not eliminated.

Since DFO, similar to other metal chelators, has a strong Fe-III binding constant ($10^{31}$), it is rapidly eliminated from the blood and does not readily cross the blood-brain barrier. Thus, when metal chelator-based therapeutic agents are administered intravenously, orally or even intranasally—but not directly to the upper one-third of the nasal cavity—to target affected tissues within the brain, the therapeutic effect has been heretofore minimal. Delivery of intranasal DFO to the upper one-third of the nasal cavity has been assessed by administering 6 mg DFO bound to 6 µCi of $^{59}$Fe (as $^{59}$FeCl$_3$) to rats under anesthesia. The IN dose in 60 µL was administered as 6 µL drops over twenty minutes. Following delivery, tissues were removed for analysis. Using scintillation counting, labeled ferrioxamine was detected throughout the brain, with high concentrations detected in the olfactory bulbs, anterior olfactory nucleus, hypothalamus, frontal cortex and cervical spinal cord. Even higher ferrioxamine concentrations were observed in the trigeminal nerves and ventral dura. Peripheral tissues with the highest ferrioxamine concentrations included the olfactory epithelium, thyroid and cervical lymph nodes. By contrast, the blood concentrations of ferrioxamine, taken at 5 minute intervals from dosing up to 25 minutes post-dose, are quite low, indicating a minimization of exposure of the therapeutic agent to non-target tissue. The data provided in Table 1 below, thus illustrates that intranasal DFO, the concentrations having been calculated based on an extrapolation of the ferrioxamine concentration, administered to the upper one-third of the nasal cavity, is effectively delivered to the brain and upper spinal cord, with minimal systemic exposure.

TABLE 1

Intranasal Delivery of DFO
(uM concentrations in tissues @ 25 minutes after the onset of delivery)

| uL delivered | 62 | 65 | 60 | 60 | 64 | 62 | 62 | 62 | 66 | 61 |
| --- | --- | --- | --- | --- | --- | --- | --- | --- | --- | --- |
| uCi delivered | 36.55 | 38.40 | 35.45 | 35.35 | 36.77 | 35.28 | 35.30 | 34.72 | 35.80 | 34.31 |
| mg delivered | 6.15 | 6.44 | 5.95 | 5.95 | 6.29 | 6.05 | 6.05 | 6.07 | 6.45 | 6.00 |
| nmol delivered | 9,361.73 | 9,801.65 | 9,063.49 | 9,053.64 | 9,583.97 | 9,218.26 | 9,207.99 | 9,237.98 | 9,824.75 | 9,128.91 |
| Drug Delivery Time | 21 | 21 | 20 | 18 | 20 | 22 | 20 | 20 | 20 | 18 |
| Time of Perfusion | 25 | 25 | 26 | 27 | 25 | 26 | 27 | 26 | 26 | 26 |
| Rat weight | 303 | 302 | 264 | 281 | 298 | 309 | 336 | 283 | 318 | 315 |
| RAT # | DF09 | DF10 | DF11 | DF12 | DF13 | DF14 | DF15 | DF18 | DF19 | DF20 |
| Blood Sample 1 (5:00) | 1.2 | 1.6 | 0.6 | 1.2 | 0.7 | 1.5 | 1.1 | 0.8 | 0.3 | 1.8 |
| Blood Sample 2 (10:00) | 1.1 | 2.1 | 1.1 | 1.2 | 1.2 | 1.8 | 1.7 | 1.0 | 0.4 | 1.9 |
| Blood Sample 3 (15:00) | 1.1 | 2.0 | 0.5 | 1.8 | 0.9 | 1.4 | 1.7 | 1.3 | 0.5 | 2.6 |
| Blood Sample 4 (20:00) | 1.1 | 1.8 | 0.3 | 1.9 | 1.1 | 1.6 | 1.5 | 1.1 | 0.4 | 2.9 |

TABLE 1-continued

Intranasal Delivery of DFO
(uM concentrations in tissues @ 25 minutes after the onset of delivery)

| | | | | | | | | | | |
|---|---|---|---|---|---|---|---|---|---|---|
| Blood Sample 5 (25:00) | 1.8 | 1.6 | 1.8 | 1.3 | 1.5 | 2.2 | 1.7 | 1.3 | 0.5 | 2.1 |
| Superficial Nodes (4) | 3.4 | 0.9 | 0.6 | 0.9 | 2.2 | 0.6 | 1.8 | 0.6 | 1.1 | 0.8 |
| Cervical Nodes (2) | 12.9 | 10.9 | 34.2 | 40.8 | 58.2 | 51.4 | 65.1 | 13.2 | 11.4 | 8.1 |
| Dorsal Dura | 26.5 | 11.4 | 7.4 | 14.1 | 16.6 | 32.0 | 8.0 | 5.9 | 35.8 | 5.1 |
| Ventral Dura | 25.3 | 38.7 | 70.9 | 17.7 | 58.3 | 44.0 | 51.5 | — | 62.8 | 11.6 |
| Trigeminal Nerve | 33.3 | 14.7 | 22.4 | 8.4 | 72.8 | 25.1 | 26.6 | 17.4 | 27.0 | 9.5 |
| Olfactory Bulbs | 12.7 | 10.6 | 30.0 | 14.7 | 20.5 | 13.1 | 28.0 | 27.5 | 21.6 | 6.6 |
| Anterior Olfactory Nucleus | 4.4 | 4.2 | — | — | 5.4 | 2.5 | 5.5 | 4.4 | 7.7 | — |
| Frontal Cortex | 4.3 | 3.3 | 13.6 | — | 2.5 | 1.1 | 6.5 | 1.4 | 5.0 | — |
| Caudate/Putamen | 2.0 | 1.5 | 2.1 | — | 2.4 | 0.9 | 1.6 | 1.1 | 2.0 | — |
| Septal Nucleus | 2.6 | 1.6 | 1.6 | — | 3.2 | 1.9 | 2.0 | 1.8 | 2.9 | — |
| Hippocampus | 0.9 | 0.9 | 0.9 | — | 2.3 | 1.2 | 1.2 | 0.5 | 1.3 | — |
| Parietal cortex | 1.3 | 1.6 | 2.3 | — | 0.7 | 1.9 | 2.8 | 0.8 | 1.0 | — |
| Thalamus | 1.1 | 1.2 | 1.2 | — | 1.5 | 1.0 | 1.0 | 0.8 | 1.2 | — |
| Hypothalamus | 5.4 | 7.3 | 6.5 | — | 3.1 | 3.0 | 6.1 | 2.7 | 3.8 | — |
| Midbrain | 1.3 | 1.3 | 1.1 | — | 1.8 | 1.3 | 1.2 | 0.6 | 1.3 | — |
| Pons | 2.0 | 1.5 | 1.4 | — | 1.5 | 2.0 | 2.6 | 0.7 | 2.4 | — |
| Medulla | 1.1 | 2.3 | 1.2 | — | 1.7 | 2.2 | 3.0 | 1.0 | 2.0 | — |
| Upper Cervical Spinal Cord | 2.1 | 1.4 | 3.7 | 1.5 | 3.9 | 6.8 | 7.3 | 1.4 | 4.6 | 4.6 |
| Cerebellum | 0.8 | 0.9 | 0.6 | — | 0.9 | 1.4 | 1.1 | 0.5 | 1.1 | — |
| Thyroid | 1125.4 | 2932.7 | 448.2 | 814.1 | 466.7 | 1285.4 | 753.3 | 751.4 | 3463.9 | 605.9 |
| Olfactory Epithelium | 12016.8 | 11374.8 | 11191.7 | 13841.7 | 9519.2 | 10724.4 | 11764.8 | 9572.8 | 9321.0 | 12205.2 |
| Axillary Nodes (2) | 0.5 | 0.4 | 0.3 | 0.3 | 0.4 | 0.5 | 0.3 | 0.4 | 1.0 | 3.1 |
| Liver | 0.4 | 0.8 | 0.4 | 0.3 | 0.3 | 0.3 | 0.3 | 0.4 | 0.4 | 0.4 |
| Kidney | 1.0 | 0.4 | 0.5 | 0.6 | 0.4 | 0.2 | 0.6 | 1.0 | 1.2 | 0.5 |
| Muscle | 0.4 | 0.3 | 0.3 | 0.4 | 0.4 | 0.2 | 0.6 | 0.6 | 0.7 | 0.4 |
| Heart | 0.4 | 0.4 | 0.5 | 1.6 | 0.6 | 0.3 | 2.2 | 0.2 | 0.2 | 0.5 |
| Lung | 0.6 | 1.4 | 0.7 | — | 1.0 | 0.5 | 2.2 | 1.5 | 1.1 | 0.5 |
| Lower Cervical Spinal Cord | 0.5 | 5.3 | 1.0 | 2.7 | 0.3 | 0.1 | 3.8 | 0.4 | 1.8 | 0.3 |
| Thoracic Spinal Cord | 0.1 | 0.2 | 0.2 | 0.4 | 0.1 | 0.1 | 1.2 | 0.3 | 0.6 | 0.1 |
| Lumbar Spinal Cord | 0.1 | 0.1 | 0.1 | 0.1 | 0.1 | 0.7 | 0.1 | 0.1 | 0.1 | 0.1 |
| Spinal Dura | 1.9 | 3.3 | 1.3 | 4.2 | 1.1 | 2.3 | — | 0.4 | 1.5 | 0.8 |

The method of the invention delivers the therapeutic agent to the nasal cavity of a mammal. It is preferred that the agent be delivered to the olfactory area in the upper one-third of the nasal cavity and, particularly, to the olfactory neuroepithelium in order to promote rapid and efficient delivery of the agent to the CNS along the olfactory neural pathway rather than the capillaries within the respiratory epithelium. The preferred transport of the therapeutic agent, e.g., DFO, to the brain by means of the olfactory and trigeminal neural pathways rather than the circulatory system so that the harmful side effects and potentially short half-life of the agent is not an issue. Further, certain agents may simply be unable due to size to cross the blood-brain barrier from the bloodstream into the CNS. The preferred method allows direct delivery of such molecules to the CNS. The data provided in Table 1 above strongly supports the increased efficacy of one embodiment of the inventive method.

To deliver the therapeutic agent to the CNS, the agent alone or in combination with other substances as a pharmaceutical composition may be administered to the olfactory area located in the upper one-third of the nasal cavity. The composition may be administered intranasally as a powered or liquid spray, nose drops, a gel or ointment, through a tube or catheter, by syringe, packtail, pledget or by submucosal infusion. Optimization of the administration of the therapeutic agent is provided by the various embodiments by applying the agent to the upper third of the nasal cavity.

The optimal concentration of the active therapeutic agent will necessarily depend upon the specific neurologic agent used, the characteristics of the patient and the nature of the disease or condition for which the agent is being used. In addition, the concentration will depend upon whether the agent is being employed in a preventive or treatment capacity. Further, the stage of a particular disease or disorder, e.g., early vs. late Alzheimer's disease, may dictate the optimal concentration of the agent.

Figure 1:
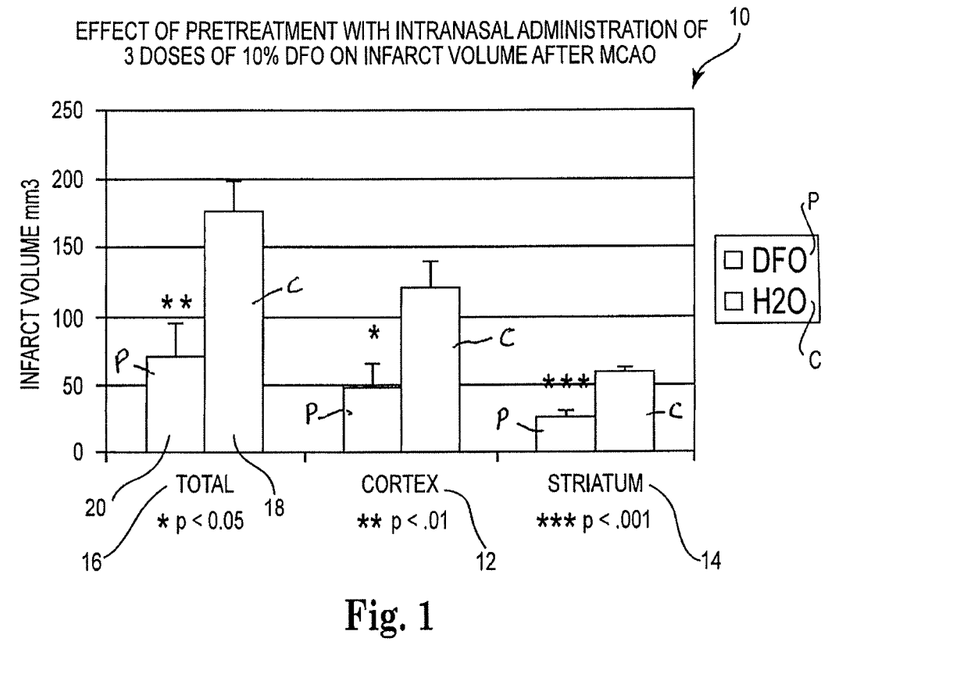
FIG. 1 is a bar graph illustrating pre-stroke treatment with intranasal administration of three doses of 10% DFO and its effect on infarct volume.

Exemplary work performed according to one embodiment of the inventive method was performed, the results of which are illustrated in FIG. 1. The experimental plan included administration of a 10% solution of DFO in distilled water in three doses of 6 mg each (in 60 µl), one dose every three hours, directly to the CNS of laboratory rats via an intranasal (IN) (upper third of naval cavity) route followed by a 2-hour middle cerebral artery occlusion (MCAO) 48 hours post-DFO administration. The animals were sacrificed 5 days after MCAO and the brains removed, sectioned on a brain matrix at 2 mm intervals and then stained with 2,3,5-triphenyltetrazolium chloride (TTC). Infarct volumes were measured using NIH Image.

Intranasal DFO reduced infarct volumes by 60% when expressed as either total infarct, cortical infarct, or striatal infarct volume. Brain proteins from olfactory bulb and from striatum were subjected to Western blot analysis for hypoxia-inducible factor-1α (HIF-1α). See FIG. 1 for a bar graph illustrating the results (10) for control animals (C) and pretreated animals (P). The results are shown broken into the cortex (12), striatum (14) and overall total (16) infarct volumes for control/pretreated animals. FIG. 1 illustrates the effectiveness of pretreating an animal with IN DFO administration of three doses of 10% DFO to the upper one-third of the nasal cavity (10), using the experimental procedure described above in connection with FIG. 1. Here, the control animals' (C) total infarct volume is 175.93 mm$^3$ (18), while the pretreated animals' (P) total infarct volume is 70.57 mm$^3$ (20). Thus, a reduction of 60% in infarct volume is realized by way of this pretreatment regimen.

Quantitation of the Western blot revealed that the amount of HIF-1α protein present in olfactory bulb and striatum was elevated approximately 30- and 20-fold, respectively. Additional brain samples from animals treated with intranasal DFO were generated, total RNA was isolated from olfactory bulb and striatum, and cDNA was generated using primers specific for HIF-1α. The cDNA was subjected to RT-PCR, and the results suggest that mRNA for HIF-1α was abundant; however, there were no differences in the concentration of HIF-1α mRNA in samples from animals treated with intranasal DFO and their controls treated with intranasal distilled water.

The data thus indicate that intranasal DFO pretreatment protects the brain during stroke via a mechanism involving the transcription factor HIF-1α and that infarct volume is significantly reduced as a result.

Figure 2:
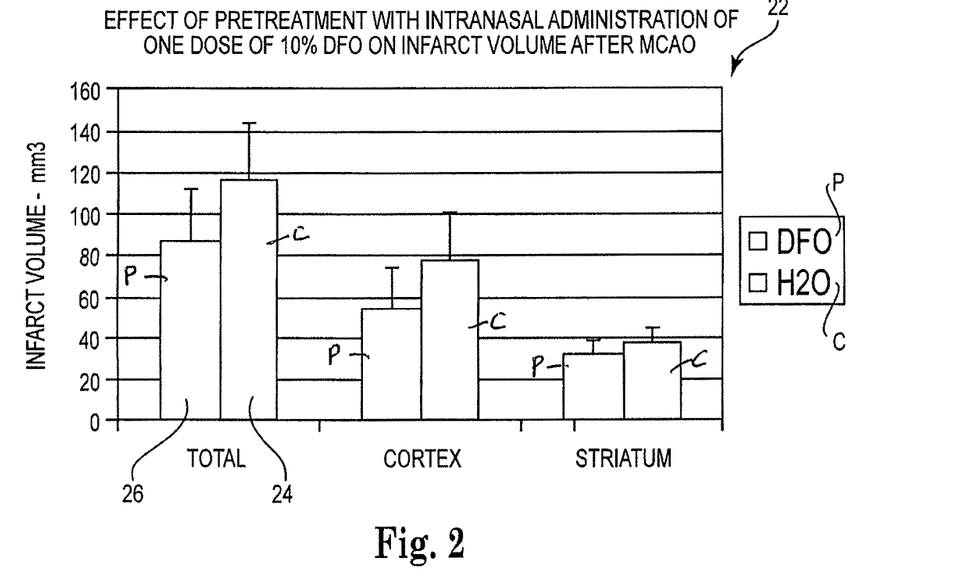
FIG. 2 is a bar graph illustrating pre-stroke treatment with intranasal administration of one dose of 10% DFO and its effect on infarct volume.

With reference to FIG. 2, data indicating the effectiveness of pretreating an animal with IN DFO administration of one dose of 10% DFO to the upper one-third of the nasal cavity (22), using the experimental procedure described above is illustrated. As illustrated, the total infarct volume is reduced, as compared with controls treated with distilled water. The control animals' (C) total infarct volume is measured at 117.28 mm$^3$ (24), while the pretreated animals' (P) infarct volume is 86.72 mm$^3$ (26), an overall infarct volume reduction of 26%.

Figure 3:
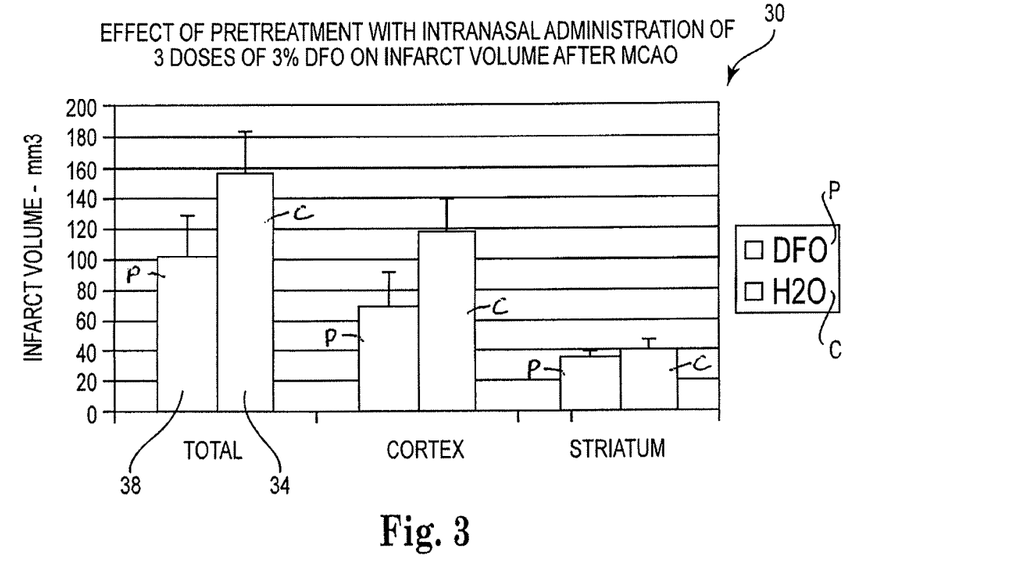
FIG. 3 is a bar graph illustrating pre-stroke treatment with intranasal administration of three doses of 3% DFO and its effect on infarct volume.

Referring now to FIG. 3, data indicating the effectiveness of pretreating an animal with IN DFO administration of three doses of 3% DFO to the upper one-third of the nasal cavity, using the experimental procedure described above is illustrated (30). Here, the control animals' (C) total infarct volume is 157.01 mm$^3$ (34), while the pretreated animals' (P) total infarct volume is measured to be 101.83 mm$^3$ (38), a reduction of 35%.

As the data presented in FIGS. 1-3 indicate, preconditioning animals by administering IN DFO, or other metal chelator, to the upper one-third of the nasal cavity significantly reduces total infarct volume. The Figures further indicate significant reduction of infarct volumes located in the Cortex and Striatum.

Thus, in one embodiment of the invention, an effective amount or dose of a metal chelator may be administered intranasally to precondition the CNS to protect a mammal against the potential of cerebral ischemia resulting from, e.g., coronary artery bypass graft (CABG) surgery. The administration of an effective amount of a metal chelator in the upper one-third of the nasal cavity eliminates the unwanted and potentially lethal side effects of DFO, for example, possible shock and rapid elimination, while providing the agent with virtually instant access to the CNS. Other metal chelating agents may have similar unwanted systemic effects. The metal chelator acts to increase the HIF-1α subunit concentration and stability of the HIF-1α subunits in the CNS. In this manner, the metal chelator performs to condition, or precondition, the CNS in anticipation of possible cerebral ischemia resulting from the CABG surgery; establishing a neuroprotective state against a future episode of cerebral ischemia.

Several neurologic disorders may be prevented, or the effects minimized, using different embodiments of the inventive method. For example, patients at risk for Alzheimer's disease may be aided by the technique, as this disease involves neurodegeneration, preceded by cerebral vascular difficulties. See, e.g., The Lancet Neurology, vol. 3, pp. 184-190, Jack C. de la Torre (March, 2004). Thus, patients at risk for Alzheimer's disease may be pretreated using one or more of the inventive embodiments disclosed herein.

Further, in another embodiment, those patients scheduled for coronary artery bypass graft (CABG) surgery may also benefit due to the relatively high percentage of post-surgical cerebral ischemia.

In another embodiment, patients at risk for Parkinson's disease may benefit from the inventive method.

In yet another embodiment patients at risk for stroke may be aided by the inventive method. Such patients would include those having risk factors comprising hypertension, diabetes, obesity, smoking, antiphospholipid syndrome or with a history of stroke (thus prone to subsequent stroke).

The above embodiments essentially focus on prevention of the cognitive, behavioral and physical impairment due to cerebral ischemia as a result of certain episodes, disorders or medical procedures by pretreatment using IN administration of a metal chelator, e.g., DFO to the upper one-third of the nasal cavities. A series of alternate embodiments focus on treating and/or minimizing the effects of such disorders after they have been diagnosed.

Figure 4:
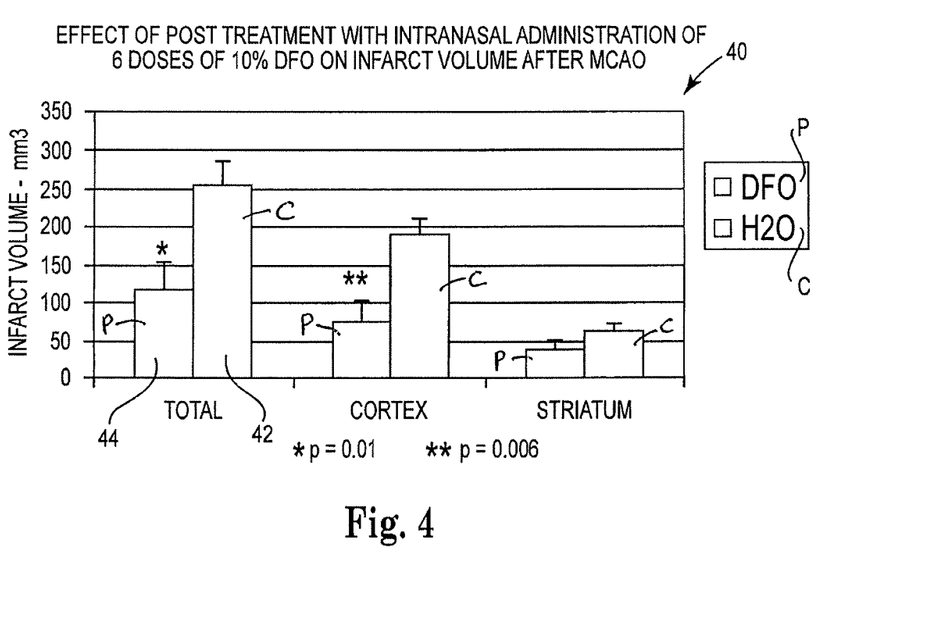
FIG. 4 is a bar graph illustrating post-stroke treatment with intranasal administration of six doses of 10% DFO and its effect on infarct volume.

In this regard, let us now turn to FIG. 4. Here, the experimental method is as follows: The method is the same as described above in connection with FIG. 1, except that the subjects are not pretreated. Instead, IN DFO is administered to the upper one-third of the nasal cavity at the start of reperfusion to treat the subjects. Six doses of 10% DFO (6 mg DFO/dose) were administered in this manner; three doses of 10% DFO at 2-hour intervals on the day of surgery and the remaining three doses of 10% DFO at three-hour intervals on the day following surgery (40). Examination of the patient brains reveals that the total infarct volume was 257 mm$^3$ (42) in the control animals (C) (treated with distilled water) and 116 mm$^3$ (44) in animals pretreated with IN DFO (P); a reduction of 55%.

For example, one embodiment of the inventive method may be used to treat a patient having, or recently having undergone, a stroke.

In another embodiment, the inventive method may be used in a treatment plan for patients at risk for, or diagnosed with, Alzheimer's disease.

In another embodiment, the inventive method may be used to treat patients at risk for, or diagnosed with, Parkinson's disease.

In another embodiment, the inventive method may be used to treat patients at risk for, or diagnosed with, Wilson's disease.

In another embodiment, the inventive method may be used to treat patients at risk for, or diagnosed with, traumatic brain injury, spinal cord injury or cerebral hemorrhage.

In yet another embodiment, patients at risk for, or diagnosed with, stroke and/or transient ischemic attack, and thus at risk for a subsequent stroke, may benefit from the inventive method.

Figure 5:
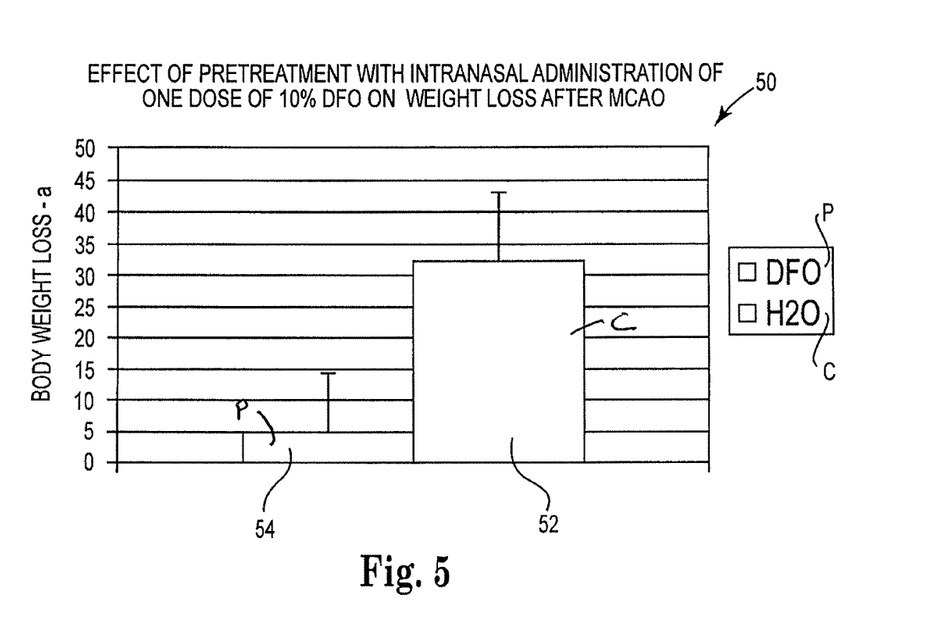
FIG. 5 is a bar graph illustrating pre-stroke treatment with intranasal administration of one dose of 10% DFO and its effect on weight loss post-stroke.

FIGS. 5-8 illustrate another embodiment of the inventive method. Patient weight loss following an ischemic episode is a nagging problem that may ultimately inhibit and slow the patient's recovery time. FIG. 5 illustrates the effect of pretreating a patient with administration of one dose of 10% IN DFO (6 mg DFO/dose) to the upper one-third of the nasal cavity has on patient weight loss post-stroke (50) using the experimental method described above in connection with FIG. 1. Here, the control subjects (C) (treated with distilled water) lost a total of 32.31 grams (52) compared with the subjects pretreated with IN DFO (P) with a weight loss of 4.60 grams (54); an 86% decrease in weight loss.

Figure 6:
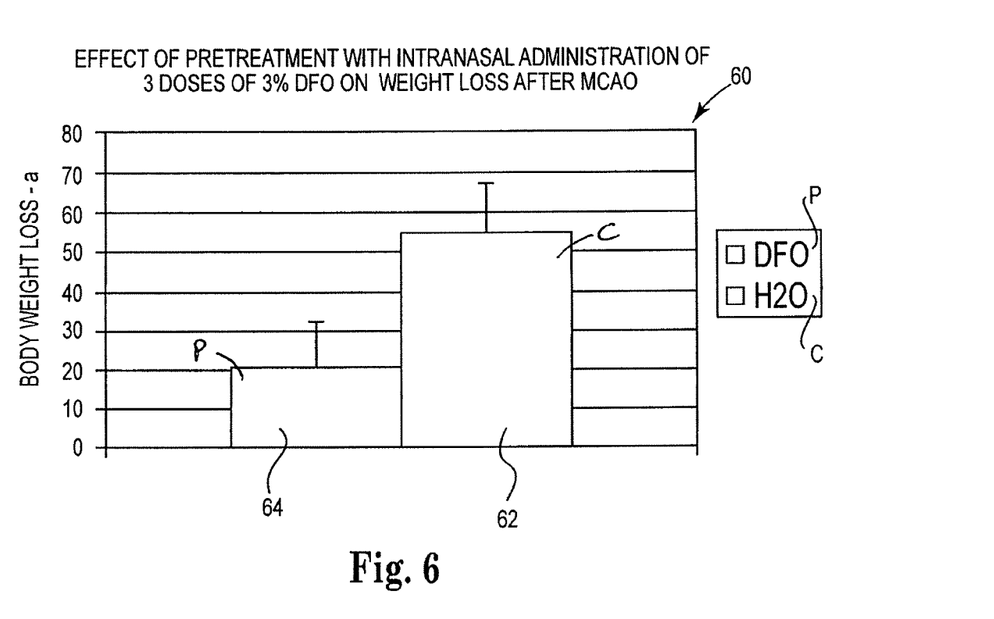
FIG. 6 is a bar graph illustrating pre-stroke treatment with intranasal administration of three doses of 3% DFO and its effect on weight loss post-stroke.

FIG. 6 illustrates the effect of pretreating a patient with administration of three doses of 3% IN DFO (6 mg DFO/dose) to the upper one-third of the nasal cavity has on patient weight loss post-stroke (60) using the experimental method described above in connection with FIG. 1. Here, the control subjects (C) (treated with distilled water) lost a total of 54.8 grams post-stroke (62) compared with the subjects pretreated with IN DFO (P) with a post-stroke weight loss of 20.5 grams (64); an 62.6% decrease in weight loss.

Figure 7:
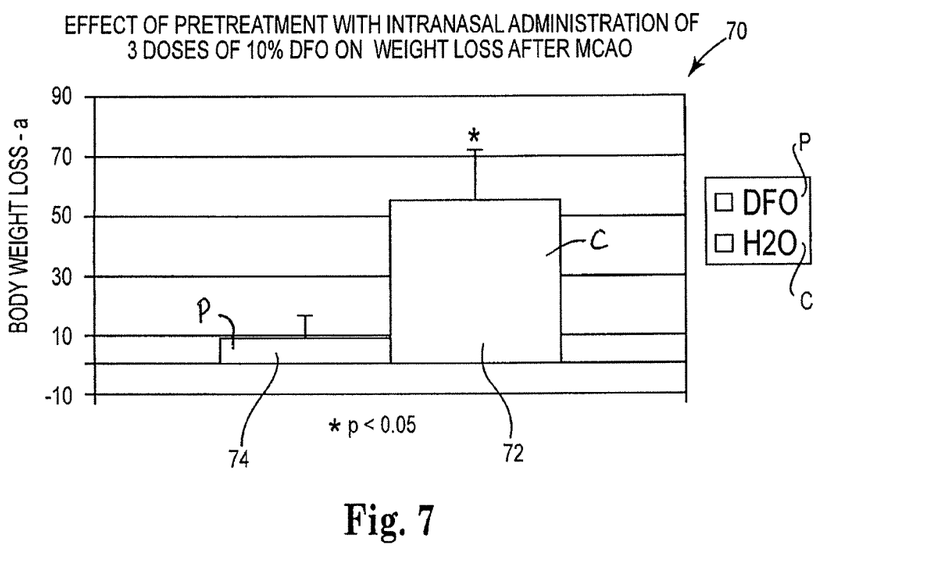
FIG. 7 is a bar graph illustrating pre-stroke treatment with intranasal administration of three doses of 10% DFO and its effect on weight loss post-stroke.

FIG. 7 illustrates the effect of pretreating a patient with administration of three doses of 10% IN DFO (6 mg DFO/dose) to the upper one-third of the nasal cavity has on patient weight loss post-stroke (70) using the experimental method described above in connection with FIG. 1. Here, the control subjects (C) (treated with distilled water) lost a total of 55.38 grams post-stroke (72) compared with the subjects pretreated with IN DFO (P) with a post-stroke weight loss of 8.44 grams (74); an 84.8% decrease in weight loss.

Figure 8:
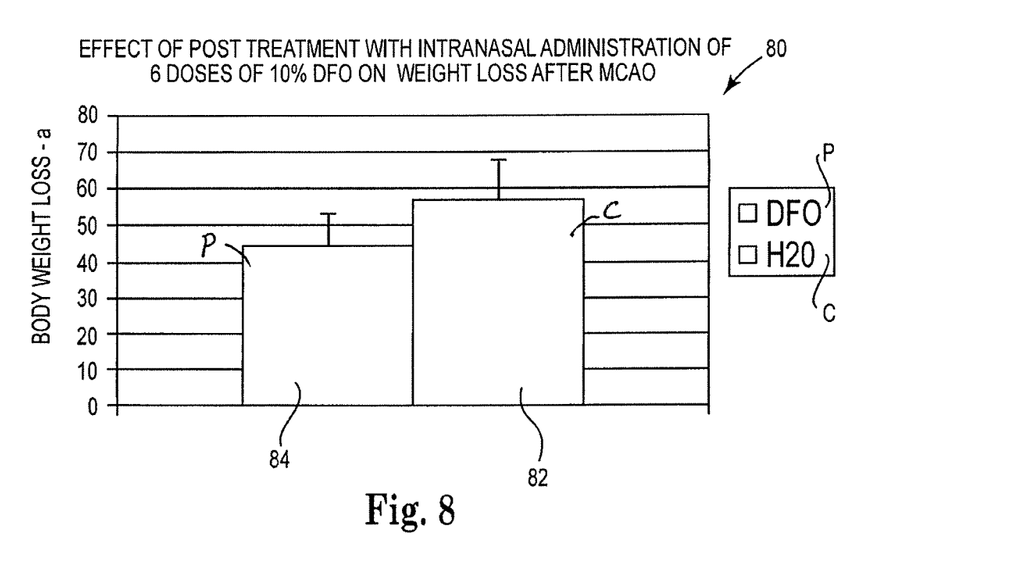
FIG. 8 is a bar graph illustrating post-stroke treatment with intranasal administration of six doses of 10% DFO and its effect on weight loss post-stroke.

FIG. 8 illustrates the effect of administering IN DFO post-stroke, as opposed to the pretreatment regimes provided in FIGS. 6-8. Here, six doses of 10% IN DFO (6 mg DFO/dose) are administered to the upper one-third of the patient's nasal cavity (80). Following stroke, the control subjects (C) (treated with distilled water) lost a total of 56.83 grams (82) compared with the subjects pretreated with IN DFO (P) with a weight loss of 44.67 grams (84); an 21.4% decrease in weight loss.

DFO is a particular example of an iron chelator that may be used in one embodiment to stimulate and/or stabilize HIF-1α to achieve the desired neuroprotective result. Other iron chelators that may be administered according to an embodiment of the method comprise compounds from the hydroxamate family, and salicylaldehyde isonicotinoyl hydrazone. Other equivalent iron chelating compounds will present themselves readily to those skilled in the art and are within the scope of the disclosure.

Alternatively, copper chelating compounds may be administered according to an embodiment of the method and comprise trientine, n-acetyl cysteine amide, tetrathiomolybdate and bi-pyridyl compounds. Other equivalent copper chelating compounds will present themselves readily to those skilled in the art and are within the scope of the disclosure.

In another embodiment, a pharmaceutical composition may be comprised of a combination of at least one iron-chelating compound. Another pharmaceutical composition may comprise a combination of at least one copper-chelating compound. Yet another embodiment of a pharmaceutical composition according to the method may comprise a combination of at least one iron-chelating compound coupled with at least one copper-chelating compound.

In still another embodiment, a pharmaceutical composition may be comprised of a combination of at least one metal-chelating compound with at least one antioxidant.

In another embodiment, a pharmaceutical composition comprised of DFO and IGF-1 may be administered.

In general, any of the therapeutic agents or pharmaceutical compositions described or referenced herein may be administered to patients or subjects under embodiments of the inventive method prior to a surgical procedure such as CABG, during such a procedure or after such a procedure.

Preferentially, the inventive method, and embodiments thereof, focuses on chelating iron and/or copper. This chelation strategy thus prevents cycling of iron and/or copper between an oxidized and a reduced state. Such cycling is highly undesirable as free radicals are formed. Free radicals and other reactive oxygen species, e.g., $H_2O_2$, HOCl and radicals such as $O_2^-$, sulfur cation, nitric oxide radical, ferryl, peroxyl, peroxynitrite, thiyl, thiylperoxyl and alkoxyl, are highly reactive and may be highly damaging to cellular components as the free radicals react. Free radical reactions may crosslink proteins, mutate DNA and peroxidize lipids. Such reactions have deleterious effects on cellular homeostasis. Thus, controlling the iron and copper ions through chelating agents reduces or eliminates such free radical damage from the oxidation/reduction cycling.

As a result, virtually any compound that prevents the cycling of iron and copper between the oxidized and reduced state may be used in different embodiments of the inventive method.

In still another embodiment, the therapeutic agent according to the inventive methods may comprise one or more of the following substances which stimulate and/or stabilize HIF-1α: insulin, IGF-I, heregulin insulin, heregulin, TGFbeta, IL-1 beta, TNFalpha, cobalt, pyruvate, oxalacetate and lactate. It is within the scope of invention to create a pharmaceutical composition combining one or more of the foregoing substances. In addition, in other embodiments, the invention may administer a pharmaceutical composition comprising at least one of the foregoing substances with at least one metal chelator. Further, a pharmaceutical composition may be comprised in another embodiment of at least one of the foregoing substances combined with at least one antioxidant.

An effective amount, as herein defined, of the therapeutic agent to be administered pursuant to embodiments of the invention is the most preferred method of expression of dosage. Such effective amount is dependent upon many factors, including but not limited to, the type of disease or condition giving rise to an anticipated cerebral ischemic episode, the patient's general health, size, age, and the nature of treatment, i.e., short-term of chronic treatment. For illustrative purposes only, exemplary treatment regimens relating generally to the therapeutic agents disclosed herein, including dosage ranges, volumes and frequency are provided below:

Efficacious dosage range: 0.0001-1.0 mg/kg.

A more preferred dosage range may be 0.005-1.0 mg/kg.

The most preferred dosage range may be 0.05-1.0 mg/kg.

The dosage volume (applicable to nasal sprays or drops) range may be 0.015 ml-1.0 ml.

The preferred dosage volume (applicable to nasal sprays or drops) range may be 0.03 ml-0.6 ml.

Generally, the treatment may be given in a single dose or multiple administrations, i.e., once, twice, three or more times daily over a period of time. For chronic disorders such as those diagnosed with, or at risk for, Alzheimer's disease, stroke or Parkinson's disease, the treatment may consist of at least one dose per day over an extended period of time. Alternatively, for those patients anticipating CABG surgery, the treatment may be a one-time dose to precondition the CNS in anticipation of potential cerebral ischemia. Such preconditioning may require more than one dose and may be administered from 12 hours to 1 week prior to the CABG surgery. Post-stroke treatment may require more than one dose which may be administered several times over the course of a day, wherein this treatment regimen may encompass a week or more.

The brain concentrations that are likely to be achieved with the dosage ranges provided above are, for a single dose: 0.1 nM-50 µM. Over the course of a multi-dose treatment plan, the maximum brain concentration may be as high as 500 µM.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A method to treat a patient with stroke comprising:
    administering at least one effective dose of deferoxamine (DFO) to the upper one-third of the patient's nasal cavity, wherein the at least one effective dose of DFO is 0.0001 to 1.0 mg/kg;
    thereby enabling at least one effective dose of DFO to bypass the patient's blood-brain barrier and delivering at least one effective dose of DFO to the patient's central nervous system; and
    treating the patient with stroke.

2. The method of claim 1, wherein the administration of the at least one effective dose of DFO treats neurodegeneration in the patient, wherein the neurodegeneration is caused by stroke.

3. The method of claim 1, wherein the administration of DFO inhibits memory loss caused by stroke.

4. The method of claim 1, wherein the administration of the at least one effective dose of DFO treats physical impairment of the patient, wherein the physical impairment is caused by stroke.

5. The method of claim 1, wherein the administration of the at least one effective dose of DFO treats behavioral impairment of the patient, wherein the behavioral impairment is caused by stroke.

6. The method of claim 1, wherein the administration of the at least one effective dose of DFO treats brain damage in the patient, wherein the brain damage is caused by stroke.

7. The method of claim 1, wherein the administration of the at least one effective dose of DFO treats weight loss in the patient, wherein the weight loss is caused by stroke.

8. The method of claim 1, wherein the administration of the at least one effective dose of DFO treats infarct volume of the patient, wherein the infarct volume is caused by stroke.

9. The method of claim 8, wherein the infarct volume caused by stroke is reduced by the administration of the at least one effective dose of DFO.

10. The method of claim 1, further comprising the at least one effective dose of DFO having a volume of 0.015 to 1.0 ml.

11. The method of claim 1, wherein the at least one effective dose of DFO is 0.005 to 1.0 mg/kg.

12. The method of claim 1, further comprising administering the at least one dose of DFO until the concentration of DFO in the patient's brain is within the range of 0.1 nM to 50 µM.

13. The method of claim 1, wherein the at least one effective dose of DFO is administered to the upper one-third of the patient's nasal cavity as one of the group consisting of: a liquid spray, a powdered spray, nose drops, a gel, and an ointment.

14. A method to treat a patient with stroke comprising:
    administering at least one effective dose of a metal chelator to the upper one-third of the patient's nasal cavity, wherein the at least one effective dose of the metal chelator is 0.0001 to 1.0 mg/kg;
    thereby enabling at least one effective dose of the metal chelator to bypass the patient's blood-brain barrier and delivering at least one effective dose of the metal chelator to the patient's central nervous system; and
    treating the stroke.

15. The method of claim 14, wherein the metal chelator comprises an iron chelator or a copper chelator.

16. The method of claim 14, wherein the administration of the at least one effective dose of the metal chelator treats neurodegeneration in the patient, wherein the neurodegeneration is caused by stroke.

17. The method of claim 14, wherein the administration of the at least one effective dose of the metal chelator inhibits memory loss caused by stroke.

18. The method of claim 14, wherein the administration of the at least one effective dose of the metal chelator treats physical impairment of the patient, wherein the physical impairment is caused by stroke.

19. The method of claim 14, wherein the administration of the at least one effective dose of the metal chelator treats behavioral impairment of the patient, wherein the behavioral impairment is caused by stroke.

20. The method of claim 14, wherein the administration of the at least one effective dose of the metal chelator treats brain damage in the patient, wherein the brain damage is caused by stroke.

21. The method of claim 14, wherein the administration of the at least one effective dose of the metal chelator treats weight loss in the patient, wherein the weight loss is caused by stroke.

22. The method of claim 14, wherein the administration of the at least one effective dose of the metal chelator treats infarct volume of the patient, wherein the infarct volume is caused by stroke.

23. The method of claim 22, wherein the infarct volume caused by stroke is reduced by the administration of the at least one effective dose of the metal chelator.

24. The method of claim 14, further comprising the at least one effective dose of the metal chelator having a volume of 0.015 to 1.0 ml.

25. The method of claim 14, wherein the at least one effective dose of the metal chelator is 0.005 to 1.0 mg/kg.

26. The method of claim 14, further comprising administering the at least one dose of the metal chelator until the concentration of the metal chelator in the patient's brain is within the range of 0.1 nM to 50 µM.

27. The method of claim 14, wherein the at least one effective dose of the metal chelator is administered to the upper one-third of the patient's nasal cavity as one of the group consisting of: a liquid spray, a powdered spray, nose drops, a gel, and an ointment.

* * * * *